United States Patent
Kozam

Patent Number: 5,169,034
Date of Patent: Dec. 8, 1992

[54] FLUID DISPENSING APPARATUS WITH PULSED STREAM

[76] Inventor: George Kozam, 234 Clinton Ave., Tenafly, N.J. 07670

[21] Appl. No.: 653,405

[22] Filed: Feb. 4, 1991

[51] Int. Cl.$^5$ .......................................... B65D 37/00
[52] U.S. Cl. .................................. 222/211; 222/212; 222/482; 239/99; 239/327; 128/66
[58] Field of Search ............. 222/209, 211, 212, 213, 222/214, 215, 391, 482; 239/101, 99, 327; 433/89; 128/66; 604/212, 216, 217

[56] References Cited

U.S. PATENT DOCUMENTS

| | | | |
|---|---|---|---|
| 172,161 | 1/1876 | Parsons | 222/501 |
| 1,752,085 | 3/1930 | Hinkle | 222/214 |
| 3,199,510 | 8/1962 | Sinai | 128/66 |
| 3,229,865 | 1/1966 | Heisler et al. | 222/391 |
| 3,293,749 | 12/1966 | George et al. | 222/391 |
| 3,474,936 | 10/1969 | McDonnell | 222/212 |
| 3,635,375 | 1/1972 | Gaetke | 222/94 |
| 3,936,334 | 2/1976 | Kushida et al. | 222/95 X |
| 4,098,434 | 7/1978 | Uhlig | 222/94 |
| 4,099,548 | 7/1978 | Sturm et al. | 222/391 |
| 4,147,278 | 4/1979 | Uhlig | 222/94 |
| 4,177,939 | 12/1979 | Thomas | 222/214 |
| 4,286,735 | 9/1981 | Sneider | 222/215 |
| 4,340,157 | 7/1982 | Darner | 222/215 |
| 4,365,752 | 12/1982 | Waisbren et al. | 128/66 X |
| 4,557,401 | 12/1985 | Hodge | 222/213 |
| 4,585,149 | 4/1986 | Zulauf | 222/94 |
| 4,641,766 | 2/1987 | Vlasich | 222/391 |
| 4,763,815 | 8/1988 | Von Schuckmann et al. | 222/391 |
| 4,805,805 | 1/1989 | Ocheskey | 222/391 |
| 4,813,602 | 3/1989 | Corey | 239/101 |
| 4,821,924 | 4/1989 | Kozam | 222/211 |
| 4,892,427 | 1/1990 | Ford | 222/391 |

FOREIGN PATENT DOCUMENTS

| | | | |
|---|---|---|---|
| 3618398 | 12/1987 | Fed. Rep. of Germany | 222/391 |
| 3618399 | 12/1987 | Fed. Rep. of Germany | 222/391 |
| 1047730 | 12/1953 | France | 222/214 |
| 2355732 | 1/1978 | France | 222/214 |
| 0084848 | 3/1989 | Japan | 222/214 |
| 182658 | 7/1922 | United Kingdom | 222/214 |

*Primary Examiner*—Andres Kashnikow
*Assistant Examiner*—Kenneth Bomberg
*Attorney, Agent, or Firm*—Roger S. Thompson

[57] ABSTRACT

A fluid dispenser includes a resilient housing having opposing walls. A conduit leads from the interior of the housing to its exterior, and may be used to conduct the fluid from the interior of the housing to its desired end location. A serrated member is affixed to the interior of one of the opposing walls, and a pin is affixed to the other wall. When pressure is exerted on the opposing walls, the pin slides along the serrations of the serrated member, causing an interruption of the continuous pressure exerted on the walls, thereby causing the fluid to be delivered in a pulsed stream.

6 Claims, 1 Drawing Sheet

FLUID DISPENSING APPARATUS WITH PULSED STREAM

BACKGROUND OF THE INVENTION

The present invention relates to fluid dispensing apparatus, and, more particularly, to fluid dispensing apparatus providing fluid in a pulsed stream.

Fluid dispensing apparatus are well known. Many types of apparatus are used in varying applications. One such device is described in my earlier patent, U.S. Pat. No. 4,821,924, for a Flexible Container Having a Compression Limiting Device, the disclosure of which is hereby incorporated by reference. Such containers have widespread utility, but also have particular utility in the area of irrigating periodontal pockets. This device is useful, but has one limitation. It dispenses fluid in a substantially continuous stream. In some applications, it would be useful to dispense fluid in pulsed stream.

One application, towards which my earlier patent was also directed, is in the area of the treatment of periodontal pockets. Periodontal pockets accumulate debris, and must be cleaned on a regular basis. Some of the accumulated debris may be difficult to dislodge with a steady stream of fluid. However, delivering the fluid in a pulsed stream may dislodge such debris. In addition, a pulsed stream may have salutary massaging effects. It would be useful to provide an improved fluid dispensing device which could deliver such a pulsed stream of fluid.

Many other dispensing devices are known, as well, for delivering measured amounts of fluids. For example, U.S. Pat. Nos. 3,229,865; 3,293,749; 4,099,548; 4,641,766; 4,763,815 and 4,892,427 disclose various devices for dispensing metered amounts of fluids. However, they are not well suited to deliver a pulsed stream of fluid. They are merely useful in delivering a single, metered, pulse of a fluid, not a stream of such pulses.

OBJECTS AND SUMMARY OF THE INVENTION

Accordingly, it is an object of the invention to provide a fluid dispensing device which overcomes the drawbacks of the prior art.

It is a further object of the invention to provide a fluid dispensing device which is capable of dispensing fluid in a pulsed stream.

Briefly stated, there is provided a fluid dispenser which includes a resilient housing having opposing walls. A conduit leads from the interior of the housing to its exterior, and may be used to conduct the fluid from the interior of the housing to its desired end location. A serrated member is affixed to the interior of one of the opposing walls, and a pin is affixed to the other wall. When pressure is exerted on the opposing walls, the pin slides along the serrations of the serrated member, causing an interruption of the continuous pressure exerted on the walls, thereby causing the fluid to be delivered in a pulsed stream.

In accordance with these and other objects of the invention, there is provided a dispenser for dispensing a fluid, the dispenser comprising: a resilient housing for holding the fluid, the housing including opposing walls defining an interior and an exterior of the housing; a conduit having a first end disposed within the interior of the housing, and a second end disposed on the exterior of the housing; the fluid being dispensable from the housing through the conduit by means of pressure exerted on the opposing walls; and means for interrupting the pressure, whereby the fluid may be dispensed from the housing, through the conduit, in a pulsed stream.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
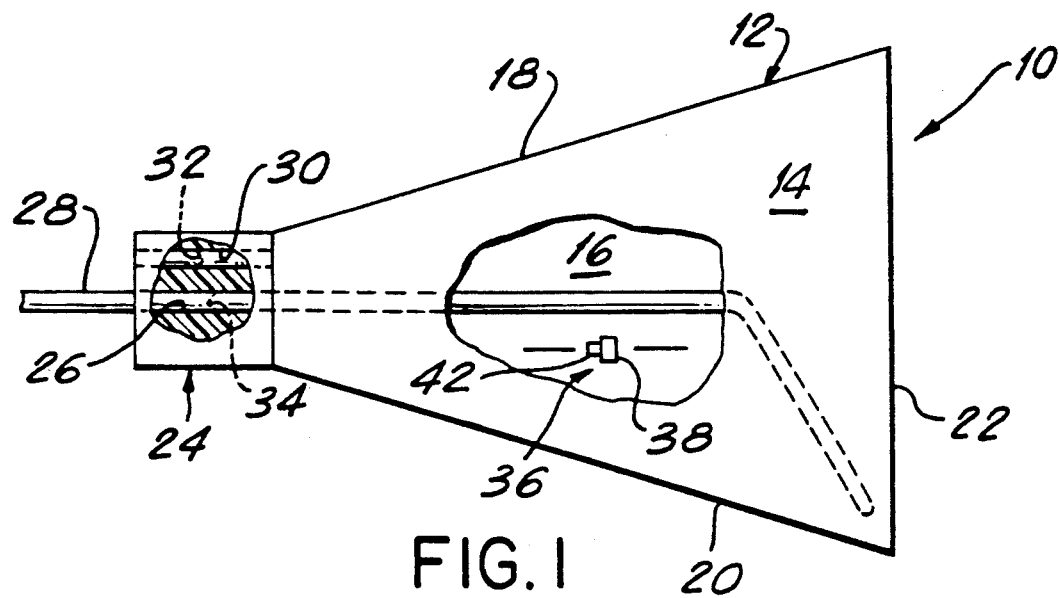
FIG. 1 is a side elevation of the preferred embodiment of the invention, shown partly in section.

Referring now to FIG. 1, there is shown, generally at 10, a fluid dispensing device in accordance with the invention. Fluid dispensing device 10 comprises a resilient housing 12, having resilient opposing walls 14 and 16, top and bottom walls 18 and 20, respectively, and a base 22. A fluid to be dispensed (not shown, for ease of illustration) is contained within housing 12.

A top 24 is affixed to housing 12 opposite base 22. Top 24 includes a first opening 26 in which a conduit 28 is disposed, and a second opening 30 in which a one-way valve 32 is disposed. One-way valve 32 is oriented to permit air flow from the exterior of housing 12 to the interior thereof, for reasons to be discussed in detail below.

Conduit 28 extends from the interior of housing 12, through top 24, to the exterior of housing 12, and includes a one-way valve 34 oriented to permit fluid flow from the interior of housing 12 to the exterior thereof.

Thus far, the construction and operation of fluid dispensing device 10 is substantially similar to those of the device disclosed in my earlier referenced patent. In short, pressure exerted on opposing walls 14 and 16 causes the fluid to be dispensed to flow through conduit 28 to the exterior of housing 12. The amount of fluid dispensed is proportional to the pressure exerted on walls 14 and 16.

After fluid flows through conduit 28 to the exterior of housing 12, and is dispensed, the pressure is released from the sides of walls 14 and 16. The resilient nature of walls 14 and 16 causes them to move apart, which results in a partial vacuum within housing 12. This vacuum pulls air through one-way valve 32 into housing 12. The process may be repeated until all of the fluid is dissipated.

Figure 2:
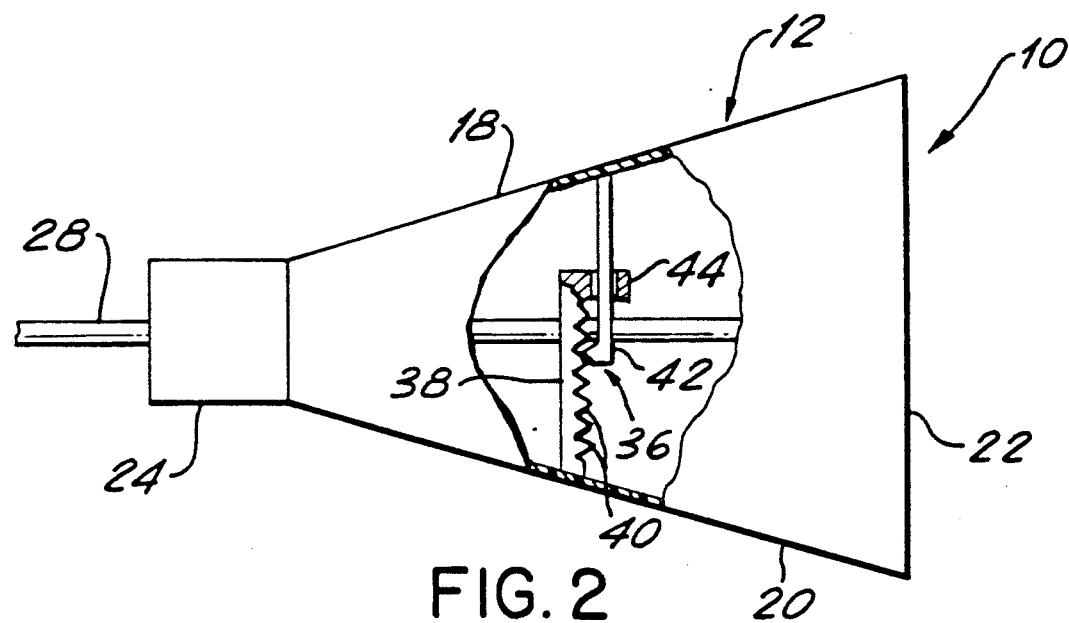
FIG. 2 is a side elevation of the preferred embodiment of the invention shown partly in section taken along lines II—II of FIG. 1.
Figure 3:
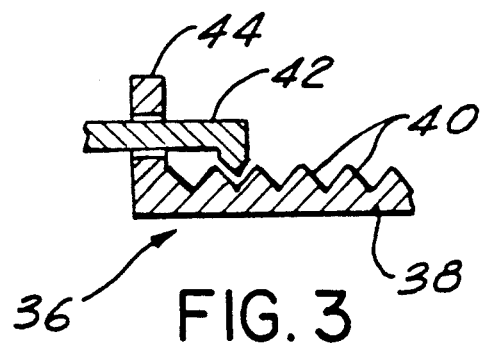
FIG. 3 is a detail of the interrupting means of the preferred embodiment of FIG. 2.

The improvement to my prior device is in the provision of an interrupting means 36 within housing 12. Interrupting means 36 is shown in detail in FIG. 2, and comprises basically two elements: a serrated member 38, having a plurality of serrations 40, and a pin 42. Serrated member 38 and pin 42 are affixed to opposing ones of walls 14 and 16.

In operation, interrupting means 36 serves to interrupt the smooth flow of fluid through conduit 28. Pressure exerted on opposing walls 14 and 16 is usually applied smoothly, and tends to urge walls 14 and 16 together in a generally continuous fashion. However, by the introduction of interrupting means 36 between walls 14 and 16, a continuous pressure exerted on walls 14 and 16 is translated to a discontinuous pressure exerted on the fluid within housing 12, since there is a variable resistance to the pressure applied to walls 14 and 16 by the sliding of pin 42 up and down serrations 40. The discontinuous pressure within housing 12 results in a pulsed flow of fluid through conduit 28.

The pulsed flow will permit the user to dislodge any particles that may have accumulated, and may also provide the added benefit of massage to the afflicted periodontal pocket under treatment, thereby speeding recovery.

To avoid the possibility of slippage between serrated member 38 and pin 42, an optional guide 44 may be attached to serrated member 38, to guide pin 42 in its travel across serrations 40, thereby ensuring that pin 42 maintains contact with serrations 40.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A dispenser for dispensing a fluid, said dispenser comprising:

a resilient housing for holding said fluid, said housing including opposing walls defining an interior and an exterior of said housing;

a conduit having a first end disposed within said interior of said housing, and a second end disposed on said exterior of said housing;

said fluid being dispensable from said housing through said conduit by means of pressure exerted on said opposing walls; and means for repeatedly interrupting said pressure thereby dispensing said fluid from said housing, through said conduit, in a repeatedly pulsed continuous stream.

2. The dispenser of claim 1, wherein said means for interrupting includes a serrated member affixed to one of said opposing walls.

3. The dispenser of claim 2, wherein said means for interrupting further includes a pin for engaging said serrated member, whereby relative movement between said serrated member and said pin is discontinuous, by the interaction of said pin sliding along said serrated member.

4. The dispenser of claim 3, wherein said pin is affixed to one of said opposing walls, opposite to said serrated member.

5. The dispenser of claim 2, wherein said serrated member includes regularly spaced serrations.

6. The dispenser of claim 4, further comprising:

a guide, affixed to said serrated member, for maintaining said pin in contact with said serrated member.

* * * * *